United States Patent [19]

Tada et al.

[11] Patent Number: 5,527,798
[45] Date of Patent: Jun. 18, 1996

[54] PYRIDAZINONE DERIVATIVES, AND INSECTICIDAL AND MITICIDAL COMPOSITION

[75] Inventors: Isao Tada, Tokushima; Hisashi Takao, Tokushima, both of Japan

[73] Assignee: Otsuka Kaguku Kabushiki Kaisha, Osaka, Japan

[21] Appl. No.: 256,732
[22] PCT Filed: Dec. 1, 1993
[86] PCT No.: PCT/JP93/01745
§ 371 Date: Jul. 29, 1994
§ 102(e) Date: Jul. 29, 1994
[87] PCT Pub. No.: WO/9412479
PCT Pub. Date: Jun. 9, 1994

[30] Foreign Application Priority Data

Dec. 3, 1992 [JP] Japan ................. 4-323841

[51] Int. Cl.$^6$ .................................. A01N 43/58
[52] U.S. Cl. ........................... 514/247; 544/240
[58] Field of Search ............ 504/238; 514/247; 544/240

[56] References Cited

U.S. PATENT DOCUMENTS 4,571,397  2/1986  Taniguichi .................. 504/238
5,278,163  1/1994  Ogura ......................... 544/240

FOREIGN PATENT DOCUMENTS

| 302346 | 2/1989 | European Pat. Off. . | |
| 63-215674 | 9/1988 | Japan | 544/239 |
| 3-220177 | 9/1991 | Japan . | |
| 6-12479 | 9/1994 | Japan | 544/241 |
| 61-17570 | 2/2986 | Japan . | |

*Primary Examiner*—Ronald G. Daus
*Attorney, Agent, or Firm*—Armstrong, Westerman, Hattori, McLeland & Naughton

[57] ABSTRACT

The invention provides a pyridazinone derivative having a high insecticidal and miticidal activity against agricultural noxious insects. The pyridazinone derivative of the invention is represented by the formula (1)

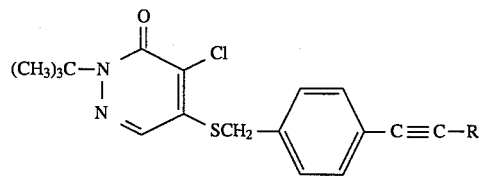

wherein R is a hydrogen atom, an alkyl group, an alkoxyalkyl group, or a phenyl group which may have 1 or 2 substituents in an optional position.

4 Claims, No Drawings

PYRIDAZINONE DERIVATIVES, AND INSECTICIDAL AND MITICIDAL COMPOSITION

TECHNICAL FIELD OF THE INVENTION

The present invention relates to novel pyridazinone derivatives, and insecticidal and miticidal compositions containing said derivatives as an active ingredient.

PRIOR ART

Of pyridazinone derivatives, some are known as effective insecticidal and miticidal compounds. For example, Japanese Unexamined Patent Publication No. 17570/1986 discloses 2-t-butyl-4-chloro-5-(4-n-hexyl)benzylthio- 3(2H)-pyridazinone, etc., and Japanese Unexamined Patent Publication No. 27736/1987 discloses 2-t-butyl- 4-chloro-5-(4-vinyl)benzylthio-3(2H)-pyridazinone, etc. However, these compounds are unsatisfactory in potency.

DISCLOSURE OF THE INVENTION

An object of the present invention is to provide a novel pyridazinone derivative having a high insecticidal and miticidal activity against various agricultural noxious insects.

In view of the foregoing situation, the inventors of the present invention conducted extensive research on pyridazinone derivatives to develop compounds having a high insecticidal and miticidal activity against various agricultural noxious insects and found that a pyridazinone derivative represented by the formula (1)

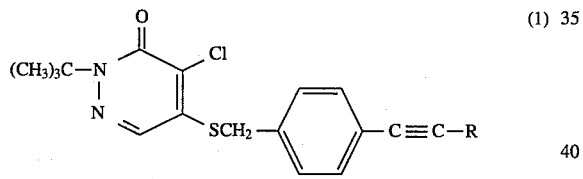

(1)

wherein R is a hydrogen atom, an alkyl group, an alkoxyalkyl group or a phenyl group which may have 1 or 2 substituents in an optional position is a novel compound undisclosed in literature and has a potent insecticidal and miticidal activity. Then the inventors confirmed that the compound of the formula (1) gives a potent killing effect on resistant vermin which have caused agricultural problems and the compound has a low toxicity. The present invention has been completed on the basis of this novel finding.

The compound of the formula (1) according to the present invention is useful as an insecticidal and miticidal agent. The compound of the invention shows a particularly high insecticidal activity against noxious insects such as those of the order Lepidoptera, e.g. Adoxophyes sp., *Plutella xylostella, Pieris rapae crucivora, Autographa nigrisigna, Spodoptera exigua, Spodoptera litura*, etc., the order Coleoptera, e.g. Cororado potato beetle, Mexican bean beetle, etc., the order Hemiptera, e.g. *Myzus persicae, Aphis gossypii, Aphis craccivora, Nephotettix cincticeps, Empoasca onukii, Laodelphax striatellus, Sogatella furcifera, Nilaparvata lugens, Trialeurodes vaporariorum, Bemisia tabaci*, etc., the order Thysanoptera, e.g. *Thrips palmi, Scirtothrips dorsalis*, etc., the order Tetranychidae, e.g. *Tetranychus urticae, Tetranychus kanzawai, Panonychus citri*, etc., the order Eriophyidae, e.g. *Aculus pelekassi*, etc., the order Tarsonemidae, e.g. *Hemitarsonemus latus*, etc.

The compound of the present invention is advantageous in effectively exterminating a wide range of vermin as compared with conventional pyridazinone derivatives. The compound of the invention displays a potent insecticidal activity also against insecticide-resistant noxious insects which conventional pyridazinone derivatives have been unable to fully control. The compound of the invention can produce an immediate insecticidal effect on, among other vermin, the order Lepidoptera such as *Plutella xylostella, Spodoptera litura*, etc.

The compound of the invention has also an activity to diminish the appetite of said vermin for food and an activity to hinder their growth.

The compound of the invention shows not only an activity to kill adults of said vermin but an effect of restraining their hatch.

Among the compounds of the invention, the pyridazinone derivatives of the formula (1) wherein R is a straight or branched chain alkyl group having 1 to 5 carbon atoms, preferably 4 carbon atoms, are desirable because they have a potent insecticidal effect on a wide range of noxious insects and other properties.

The compound of the invention is prepared by the process illustrated below by Reaction Scheme 1:

Reaction Scheme 1

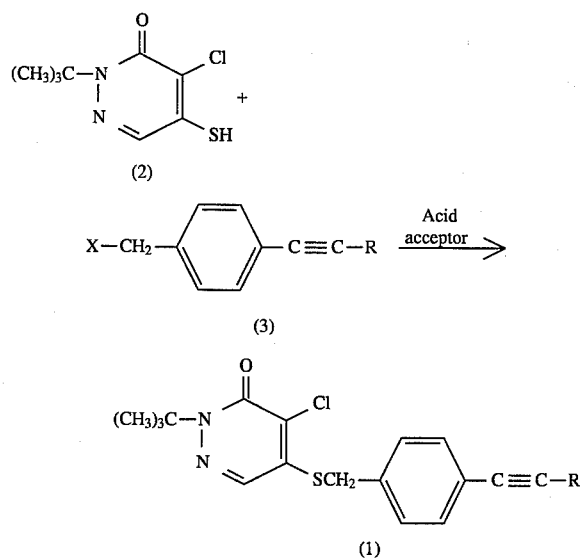

wherein R is as defined above, and X is a halogen atom.

That is, the compound of the invention is prepared by reacting a pyridazinone derivative of the formula (2) with a benzyl halide of the formula (3) in the presence of an acid acceptor. Solvents which are used in said reaction include, for example, alcohols such as methanol, ethanol, etc., hydrocarbons such as benzene, toluene, etc., ketones such as acetone, methyl ethyl ketone, etc., ethers such as tetrahydrofuran, 1,4-dioxane, etc., nitriles such as acetonitrile, propionitrile, etc., and amides such as N,N-dimethylformamide, hexamethylphosphoric triamide, etc. When required, a solvent mixture of such solvent and water can be used in the invention. As to the proportions of the pyridazinone derivative of the formula (2) and the benzyl halide of the formula (3) used in the reaction, about 0.5 to about 2 moles, preferably about 1 to about 1.5 moles, of the latter is used per mole of the former. Acid acceptors which are used in the invention include a wide variety of conventional ones. Specific examples of acid acceptors are tertiary amines such as triethylamine, pyridine, etc., salts of alkali metals such as sodium carbonate, potassium carbonate, etc., and hydroxides of alkali metals such as sodium hydroxide, potassium hydroxide, etc. The amount of such acid acceptor used is about 1 to about 2 moles, preferably about 1 to about 1.2 moles, per mole of the compound of the formula (2). The reaction advantageously proceeds at a temperature in the range of room temperature to the boiling point of the solvent used and is generally completed in about 1 to about 5 hours.

The compound of the formula (2) used as one of the starting materials in Reaction Scheme 1 is a known compound and can be easily prepared in accordance with conventional processes, e.g. the process disclosed in Angew. Chem. Internat. Edit., 4 (4), 292–300 (1965). The compound of the formula (3), i.e. the other starting material, can be easily prepared by the process illustrated below in Reaction Scheme 2:

Reaction Scheme 2

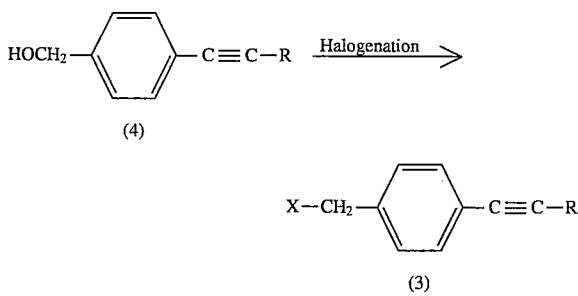

The compound of the formula (3) can be prepared in a high yield by halogenating a compound of the formula (4) in the conventional manner, for example, in the presence of a halogenating agent such as a thionyl halide, e.g. thionyl chloride and thionyl bromide, phosphorus trichloride, phosphorus tribromide and the like.

The compound of this invention prepared by the process described above can be easily isolated and purified from the reaction mixture by conventional separation methods such as solvent extraction, recrystallization, column chromatography, etc. Thus the compound of the invention can be produced in a high yield with a high purity according to the above process.

For use as an insecticidal and/or miticidal agent, the compound of the invention is made available in the form of emulsions, hydrated compositions, suspensions, fine particles, powders, wettable powders, coating compositions, foam spray preparations, microcapsules, aerosols, compositions for impregnating natural or synthetic substances, fumigants, concentrates for application in small amounts, etc. In preparing these compositions, various surfactants are usable for emulsifying, dispersing, suspending or foaming purposes. Examples of useful surfactants include nonionic surfactants such as polyoxyethylene alkyl ethers, polyoxyethylene alkyl esters, polyoxyethylene sorbitan alkyl esters and sorbitan alkyl esters, and anionic surfactants such as alkylbenzene sulfonates, alkylsulfosuccinates, alkyl sulfates, polyoxyethylene alkyl sulfates, allylsulfonates and lignin sulfite. Usable as dissolving agents, diluents and carriers are various organic solvents, aerosol propellants, natural minerals and vegetables, synthetic compounds, etc. Examples of especially preferable organic solvents are benzene, toluene, xylene, ethylbenzene, chlorobenzene, alkyl naphthalenes, dichloromethane, chloroethylene, cyclohexane, cyclohexanone, acetone, methyl ethyl ketone, methyl isobutyl ketone, alcohols, dimethylformamide, dimethyl sulfoxide, acetonitrile, naphtha, mineral oil distillates, etc. Examples of useful aerosol propellants are propane, butane, hydrocarbon halides, nitrogen, carbon dioxide, etc. Examples of useful mineral materials are kaolin, talc, bentonite, diatomaceous earth, clay, montmorillonite, chalk, calcite, pumice, meerschaum, dolomite, etc. Examples of useful vegetables are walnut shells, tobacco stalks, sawdust, etc. Examples of useful synthetic compounds are alumina, silicates, sugar polymers, etc. Examples of tackifying agents are carboxymethylcellulose, gum arabic, polyvinyl alcohol, polyvinyl acetate, etc. Such compositions can be colored with an organic or inorganic dye. The compositions described above are prepared by incorporating the compound of the invention in an amount of about 0.1 to about 95 wt. %, preferably about 0.5 to about 90 wt. %.

The compound of the invention has a higher solubility in petroleum-type organic solvents conventionally used in preparing an emulsion, such as naphtha, xylene, etc. than conventional pyridazinone derivatives. Because of this high solubility, an emulsion containing the compound of this invention in a high concentration can be provided, thereby giving an advantage in transport and storage.

The composition prepared is used as such or as diluted with a carrier or water. In conformity with the contemplated purpose, the composition can be diluted to the range of about 0.00001 to about 100 wt. % as desired. Preferably, the composition is used as diluted so as to contain about 0.0001 to about 10 wt. % of the present compound. Although the amount of the composition to be applied varies with the population of insects and mites, weather, etc. and can not be determined specifically, it is generally about 0.1 to about 10 kg, preferably about 0.1 to about 1 kg, per hectare calculated as the amount of the present compound.

BEST MODE FOR CARRYING OUT THE INVENTION

Given below are Preparation Example and Test Examples for the compounds of the invention.

Preparation Example 1

Anhydrous sodium carbonate (2.1 g, 0.015 mole) was added in small amounts to a solution of 2-t-butyl-5 -mercapto-3(2H)-pyridazinone (220 g, 0.01 mole) and 4-(2-n-butyl)ethenyl benzyl bromide (2.92 g, 0.011 mole) in methanol (20 ml) with stirring at room temperature. After the completion of addition, the reaction mixture was stirred for a further 4 hours at room temperature, followed by the addition of 200 ml of benzene and 200 ml of water. The organic layer was washed with water and dried over anhydrous magnesium sulfate. After removal of the solvent, the residue was subjected to silica gel column chromatography with benzene-ethyl acetate as an eluent, giving 3.11 g of 2 -t-butyl-4-chloro-5-[4-(2-n-butyl)ethenyl]benzylthio-3(2H)-pyridazinone as a yellow oil in a 80% yield. The properties of the obtained compound (compound No. 5) are shown below in Table 1.

Table 1 shows the properties of compounds prepared in the same manner as in Preparation Example 1.

TABLE I

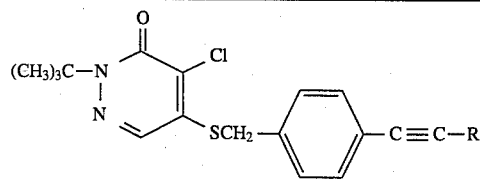

| Compound No. | R | Appearance | $^1$H-NMR (CDCl$_3$) δ ppm |
|---|---|---|---|
| 1 | CH$_3$OCH$_2$CH$_2$— | yellow oil | 1.62(9H, s), 2.24(3H, s), 3.42(3H, s), 4.02(2H, m), 4.22(2H, s), 4.30(2H, m), 7.38(4H, bs), 7.52(1H, s) |
| 2 | CH$_3$OCH$_2$— | yellow oil | 1.62(9H, s), 3.42(3H, s), 4.22(2H, s), 4.30(2H, s), 7.38(4H, bs), 7.52(1H, s) |
| 3 | C$_2$H$_5$OCH$_2$— | yellow oil | 1.32(3H, t), 1.62(9H, s), 4.02(2H, m), 4.22(2H, s), 4.30(2H, m), 7.37(4H, bs), 7.52(1H, s) |
| 4 | CH$_3$— | yellow oil | 1.62(9H, s), 2.24(3H, s), 3.42(3H, s), 4.22(2H, s), 7.38(4H, bs), 7.52(1H, s) |
| 5 | n-C$_4$H$_9$— | yellow oil | 0.7–1.8(7H, m), 1.62(9H, s), 2.22–2.58(2H, m), 4.20(2H, s), 7.30(4H, bs), 7.52(1H, s) |
| 6 | t-C$_4$H$_9$— | yellow oil | 1.32(9H, s), 1.62(9H, s), 4.22(2H, s), 7.32(4H, bs), 7.52(1H, s) |
| 7 | Phenyl | yellow oil | 1.62(9H, s), 4.24(2H, s), 7.20–7.60(9H, m), 7.52(1H, s) |
| 8 | n-C$_5$H$_{11}$— | yellow oil | 0.70–1.84(9H, m), 1.62(9H, s), 2.22, 2.58(2H, m), 4.22(2H, s), 7.30(4H, bs), 7.52(1H, s) |
| 9 | n-C$_6$H$_{13}$— | yellow oil | 0.70–1.98(11H, m), 1.62(9H, s), 2.20–2.6(2H, m), 4.22(2H, s), 7.30(4H, bs), 7.52(1H, s) |
| 10 | iso-C$_5$H$_{11}$— | yellow oil | 0.9–1.1(6H, d), 1.2–1.8(3H, m), 1.62(9H, s), 2.2–2.58(2H, m), 4.20(2H, s), 7.28(4H, bs), 7.50(1H, s) |
| 11 | n-C$_8$H$_{17}$— | yellow oil | 0.70–1.9(15H, m), 1.62(9H, s), 2.22–2.6(2H, m), 4.22(2H, s), 7.30(4H, bs), 7.62(1H, s) |
| 12 | n-C$_3$H$_7$— | yellow oil | 0.88–1.2(3H, m), 1.42–1.76(2H, m), 1.62(9H, s), 2.22–2.58(2H, m), 4.22(2H, s), 7.32(4H, bs), 7.56(1H, s) |
| 13 | iso-C$_4$H$_9$— | yellow oil | 0.90–1.18(6H, m), 1.48–1.7(1H, m), 1.62(9H, s), 2.2–2.42(2H, s), 4.22(2H, s), 7.30(4H, bs), 7.54(1H, s) |
| 14 | H | yellow oil | 1.62(9H, s), 3.04(1H, s), 4.22(2H, s), 7.30(4H, bs), 7.52(1H, s) |
| 15 | p-Methoxyphenyl | yellow oil | 1.62(9H, s), 3.88(3H, s), 4.24(2H, s), 7.20–7.58(8H, m), 7.52(1H, s) |

Test Example 1

Test on *Nephotettix cincticeps*

Each test compound was dissolved in acetone and was topically applied (drop size 0.5 μl/head) to the abdomen of female adults of *Nephotettix cincticeps* (Miyagi strain or Nakakawahara strain) using a microapplicator (product of Burkard Co., Ltd.). The Miyagi strain is a class of noxious insects which are nonresistant, namely sensitive, to organic phosphorus and carbamate insecticides. The Nakakawahara strain is a class of noxious insects which are resistant to organic phosphorus and carbamate insecticides. After the application, the insects were accommodated in a cup of plastics having a diameter of 13 cm in which a rice plant with its root portion wound with moistened cotton was placed. The cup was left to stand in an assay room (25°±1° C., humidity 40%). The mortality was determined 48 hours after treatment. Table 2 below shows the results. The numbers under the column of test compounds in Table 2 correspond to those of test compounds in Table 1. The same numbers are used in ensuing tables for the corresponding test compounds.

TABLE 2

| Test Compd. No. | Amount of compound topically applied (μg) | Mortality (%) | |
|---|---|---|---|
| | | Miyagi Strain | Nakakawahara Strain |
| 1 | 0.02 | 100 | 100 |
| 2 | 0.02 | 100 | 100 |
| 4 | 0.02 | 100 | 100 |
| 5 | 0.02 | 100 | 98 |
| 12 | 0.02 | 100 | 100 |
| A | 0.1 | 60 | 40 |
| B | 0.1 | 65 | 35 |

A: 2-t-butyl-4-chloro-5-(4-n-hexyl)benzylthio-3(2H)-pyridazinone (compound disclosed in Japanese Unexamined Patent Publication No. 17570/1986)

B: 2-t-butyl-4-chloro-5-(4-vinyl)benzylthio-3(2H)-pyridazinone (compound disclosed in Japanese Unexamined Patent Publication No. 27736/1987)

Table 2 shows that the compounds of the present invention exhibit a high insecticidal activity against *Nephotettix cincticeps* resistant to organic phosphorus and carbamate insecticides as well as against *Nephotettix cincticeps* nonresistant thereto.

Test Example 2

Test on *Plutella xylostella*

Two parts by weight of each test compound of the present invention was dissolved in 98 parts by weight of acetone. The solution was diluted to a specific concentration with an aqueous solution containing 0.04% of a spreader (product of Nihon Noyaku Co., Ltd., trademark, Shin-Linoh). The leaves of cabbages, 7×7 cm, were dipped in the resulting solution for 10 seconds. Fourth-instar larvae of *Plutella xylostella* were placed, together with the leaves thus treated, into a cup of plastics 13 cm in diameter, which was then left to stand in a thermostatic chamber maintained at 25°±1° C. The insects were checked for mortality and for emergence ratio (wing growth ratio) 2 days and 7 days after treatment, respectively. The results are shown in Table 3.

TABLE 3

| Test Compd. No. | Concentration of Test Compd. (ppm) | Mortality (%) | Emergence Ratio (%) |
|---|---|---|---|
| 1 | 100 | 100 | 0 |
| 2 | 100 | 100 | 5 |
| 5 | 100 | 98 | 0 |
| 12 | 100 | 100 | 0 |
| 13 | 100 | 100 | 0 |
| A | 400 | 37 | 90 |
| B | 400 | 40 | 88 |

Table 3 shows that the compounds of the invention have a potent insecticidal effect on the larvae of *Plutella xylostella* and possessed an activity to inhibit larvae's appetite for food and an activity to restrain larvae's growth as apparent from the low emergence ratio.

Test Example 3

Test on *Myzus persicae*

Two parts by weight of each test compound of the present invention was dissolved in 98 parts by weight of acetone. The solution was diluted to a specific concentration with an aqueous solution containing 0.04% of a spreader (product of Nihon Noyaku Co., Ltd., trademark, Shin-Linoh). The leaves of cabbages, 7×7 cm, were dipped in the resulting solution for 10 seconds. Apterous viviparous female adults of *Myzus persicae* (Naruto Y strain or Naruto R strain) were placed, together with the leaves thus treated, into a cup of plastics 9 cm in diameter. The cup was then left to stand in a thermostatic chamber maintained at 25°±1° C. The Naruto Y strain is a class of noxious insects which are nonresistant, namely sensitive, to synthetic pyrethroid, organic phosphorus and carbamate insecticides. The Naruto R strain is a class of noxious insects which are resistant to synthetic pyrethroid, organic phosphorus, and carbamate insecticides. The insects were checked for mortality 2 days after treatment. The results are shown in Table 4.

TABLE 4

| Test Compd. No. | Concentration of Test Compd. (ppm) | Mortality (%) | |
|---|---|---|---|
| | | Naruto Y Strain | Naruto R Strain |
| 1 | 50 | 100 | 88 |
| 4 | 50 | 100 | 90 |
| 5 | 50 | 100 | 98 |
| 6 | 50 | 100 | 90 |
| 9 | 50 | 100 | 92 |
| 12 | 50 | 100 | 92 |
| 13 | 50 | 100 | 96 |
| A | 400 | 53 | 0 |
| B | 400 | 60 | 0 |
| C | 50 | 60 | 0 |

C: Sunmite (trade name for pyridazinone insecticide, product of Nissan Kagaku Co., Ltd.)

Table 4 shows that the compounds of the invention have a high insecticidal activity against *Myzus persicae* resistant to organic phosphorus and carbamate insecticides as well as *Myzus persicae* nonresistant thereto.

Test Example 4

Test on *Tetranychus urticae*

Two parts by weight of each test compound of the present invention was dissolved in 98 parts by weight of acetone. The solution was diluted to a specific concentration with an aqueous solution containing 0.04% of a spreader (product of Nihon Noyaku Co., Ltd., trademark, Shin-Linoh). Adults of *Tetranychus urticae* (Naruto strain or Akita strain) were placed on kidney beans planted in pots, and the solution prepared above was sprayed onto the plant until the leaves dripped. The Naruto strain is a class of noxious insects which are nonresistant, namely sensitive, to Sunmite or Danitron. The Akita strain is a class of noxious insects which are resistant to Sunmite and Danitron. Three days after treatment, the mortality was determined. Table 5 shows the results.

TABLE 5

| Test Compd. No. | Concentration of Test Compd. (ppm) | Mortality (%) | |
|---|---|---|---|
| | | Naruto Strain | Akita Strain |
| 1 | 10 | 100 | 90 |
| 4 | 10 | 100 | 100 |
| 5 | 10 | 100 | 100 |
| 6 | 10 | 100 | 90 |
| 8 | 10 | 100 | 100 |
| 12 | 10 | 100 | 90 |
| A | 100 | 50 | 0 |
| B | 100 | 40 | 0 |
| C | 10 | 100 | 20 |

Table 5 shows that the compounds of the present invention have a high insecticidal activity against *Tetranychus urticae* resistant to Sunmite or Danitron as well as *Tetranychus urticae* nonresistant thereto.

Test Example 5

Test on *Panonychus citri*

Two parts by weight of each test compound of the present invention was dissolved in 98 parts by weight of acetone. The solution was diluted to a specific concentration with an aqueous solution containing 0.04% of a spreader (product of Nihon Noyaku Co., Ltd., trademark, Shin-Linoh). Adults of *Panonychus citri* (Naruto strain or Shizuoka strain) were placed on potted seedlings of mandalin orange, and the solution prepared above was sprayed onto the plant until the leaves dripped. The Naruto strain is a class of noxious insects which are nonresistant, namely sensitive, to Sunmite and Danitron. The Shizuoka strain is a class of noxious insects which are resistant to Sunmite and Danitron. Three days after treatment, the mortality was determined. Table 6 shows the results.

TABLE 6

| Test Compd. No. | Concentration of Test Compd. (ppm) | Mortality (%) | |
|---|---|---|---|
| | | Naruto Strain | Shizuoka Strain |
| 1 | 10 | 100 | 95 |
| 4 | 10 | 100 | 90 |
| 5 | 10 | 100 | 100 |
| 6 | 10 | 100 | 98 |
| 8 | 10 | 100 | 95 |
| 12 | 10 | 100 | 90 |
| A | 400 | 50 | 0 |
| B | 400 | 50 | 0 |
| C | 10 | 100 | 0 |

Table 6 shows that the compounds of the present invention have a high insecticidal activity against *Panonychus citri* resistant to Sunmite or Danitron as well as *Panonychus citri* nonresistant thereto.

We claim:

1. A pyridazinone compound of the formula

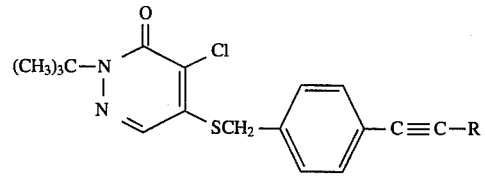

wherein R is a hydrogen atom, a lower alkyl group, a lower alkyl group, a phenyl group or a p-methoxyphenyl group.

2. A pyridazinone compound according to claim 1, wherein R is a straight chain alkyl group having 1 to 5 carbon atoms or a branched chain alkyl group having 3 to 5 carbon atoms.

3. A pyridazinone compound according to claim 1, wherein R is a straight or branched chain alkyl group having 4 carbon atoms.

4. An insecticidal and miticidal composition containing the pyridazinone compound of claim 5 as an active ingredient.

* * * * *

UNITED STATES PATENT AND TRADEMARK OFFICE
CERTIFICATE OF CORRECTION

PATENT NO.: 5,527,798
DATED : June 18, 1996
INVENTOR(S): TADA et al.

It is certified that error appears in the above-identified patent and that said Letters Patent is hereby corrected as shown below:

Title page,
    Item [73], "OTSUKA KAGUKU KABUSHIKI KAISHA" should read --OTSUKA KAGAKU KABUSHIKI KAISHA--.

Title page, Item [87], "PCT Pub. No. WO/9412479" should read --PCT Pub. No. WO94/12479--.

Signed and Sealed this

Twenty-second Day of October, 1996

Attest:

BRUCE LEHMAN

*Attesting Officer*      *Commissioner of Patents and Trademarks*